(12) United States Patent
Shiao et al.

(10) Patent No.: US 8,596,854 B2
(45) Date of Patent: Dec. 3, 2013

(54) LIGHT-GUIDE MODULE

(75) Inventors: Po-Ling Shiao, Hsinchu (TW);
Chih-Chiang Chao, New Taipei (TW);
Mei-Chun Lai, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/550,594

(22) Filed: Jul. 16, 2012

(65) Prior Publication Data
US 2013/0100663 A1    Apr. 25, 2013

(30) Foreign Application Priority Data

Oct. 21, 2011   (TW) .............................. 100138267 A (51) Int. Cl.
*F21V 7/04* (2006.01)

(52) U.S. Cl.
USPC ........... 362/621; 362/606; 362/615; 362/618; 362/627

(58) Field of Classification Search
USPC .................. 362/610, 621, 606, 607, 612, 613
See application file for complete search history.

(56) References Cited

U.S. PATENT DOCUMENTS

| | | | |
|---|---|---|---|
| 6,259,854 B1 | 7/2001 | Shinji et al. | |
| 7,226,197 B2 | 6/2007 | Hayashi et al. | |
| 7,711,223 B2 | 5/2010 | Chao et al. | |
| 7,911,700 B2 | 3/2011 | Chao et al. | |
| 8,118,464 B2 * | 2/2012 | Chang | 362/608 |
| 2004/0061440 A1 | 4/2004 | Imai et al. | |
| 2006/0152931 A1 | 7/2006 | Holman | |
| 2008/0253107 A1 * | 10/2008 | Lin | 362/84 |

FOREIGN PATENT DOCUMENTS

| | | |
|---|---|---|
| JP | 2000-249837 | 9/2000 |
| TW | 200834136 | 8/2008 |

OTHER PUBLICATIONS

Siitonen et al., "White LED light coupling into light guides with diffraction gratings," Applied Optics 45 (12), Apr. 20, 2006, pp. 2623-2630.
Lee et al., "Coupling of light from an LED into a very thin light guide by a coupling lens," Proceedings of the SPIE 6828, Nov. 12, 2007, pp. 68280K-1-68280K-7.
Lee et al., "LED Light Coupler Design for a Ultra Thin Light Guide," Journal of the Optical Society of Korea 11 (3), Sep. 2007, pp. 113-117.
Siitonen et al., "A double-sided grating coupler for thin light guides," Optics Express 15 (5), Mar. 5, 2007, pp. 2008-2018.
Siitonen et al., "Coupling of light from an LED into a thin light guide by diffractive gratings," Applied Optics 43 (30), Oct. 20, 2004, pp. 5631-5636.

(Continued)

*Primary Examiner* — Evan Dzierzynski
(74) *Attorney, Agent, or Firm* — Jianq Chyun IP Office (57) ABSTRACT

A light-guide module including a light-guide sheet and a light source is provided. The light-guide sheet includes a light-emergent region and a plurality of localized micro-structures located at a first surface of the light-guide sheet, wherein the localized micro-structures are distributed except the light-emergent region. The localized micro-structures include a plurality of arc grooves disposed on a first region. The light source includes a plurality of light-emitting devices. A light-emergent area of each of the light-emitting devices is A. In the localized micro-structures of the first region covered by the light-emitting devices, an area occupied by the arc grooves having aspect ratios greater than 0.5 is greater than or substantially equal to 0.5 A.

15 Claims, 11 Drawing Sheets

(56) References Cited

OTHER PUBLICATIONS

Ulrich et al., "Geometrical Optics in Thin Film Light Guides," Applied Optics 10 (9), Sep. 1971, pp. 2077-2085.

Murata et al., "Input couplers for thin light-guides and light-emitting diodes," Optical Engineering 47 (2), Feb. 2008, pp. 027001-1-027001-7.

* cited by examiner

LIGHT-GUIDE MODULE

CROSS-REFERENCE TO RELATED APPLICATION

This application claims the priority benefit of Taiwan application serial no. 100138267, filed on Oct. 21, 2011. The entirety of the above-mentioned patent application is hereby incorporated by reference herein and made a part of this specification.

BACKGROUND OF THE DISCLOSURE

1. Field of the Disclosure

The disclosure relates to a light-guide module.

2. Description of Related Art

In a conventional light-guide module, light provided by a linear light source generally enters a light-guide plate through a side light incident surface of the light-guide plate, and is output from a light-emergent surface of the light-guide plate, so as to provide a planar light source. Since the light provided by the light source enters the light-guide plate from the side light incident surface of the light-guide plate, a driving circuit of the light source is generally configured at a side of the light-guide plate to facilitate assembling and mass production of the light-guide module. However, in order to further decrease a whole thickness of the light-guide module to achieve a certain degree of flexibility of the light-guide module, an area of the side light incident surface of the light-guide plate is decreased as the thickness of the light-guide plate decreases, and now an amount of the light entering the light-guide plate through the side light incident surface is insufficient, which may decrease output efficiency of the light-guide module. Obviously, according to a conventional technique, a light source in a light-guide module is fixed by an external frame, and the light emitted by the light source enters a light-guide plate through a side light incident surface of the light-guide plate. Considering the output efficiency of the light-guide module, a thickness of the light-guide module of the conventional technique cannot be too small, so that the light-guide module is not easy to have flexibility.

Accordingly, how to further decrease the whole thickness of the light-guide module without greatly decreasing the output efficiency of the light-guide module is one of important issues to be developed.

SUMMARY OF THE DISCLOSURE

The disclosure provides a light-guide module including a light-guide sheet and a light source. The light-guide sheet includes a light-emergent region and a plurality of localized micro-structures, where the light-emergent region and the localized micro-structures are located on a first surface of the light-guide sheet, and the localized micro-structures are distributed except the light-emergent region. The localized micro-structures include a first region and have a plurality of arc grooves. The light source includes a plurality of light-emitting devices disposed on the first surface, lights emitted from the light-emitting devices enter the light-guide sheet through the localized micro-structures, and a light-emitting area of each of the light-emitting devices is A, and in the localized micro-structures of the first region covered by the light-emitting devices, an area occupied by the arc grooves having aspect ratios greater than 0.5 is substantially greater than or substantially equal to 0.5 A.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DETAILED DESCRIPTION OF DISCLOSED EMBODIMENTS

The disclosure is directed to a light-guide module having good output efficiency and flexibility.

First Embodiment

Figure 1:
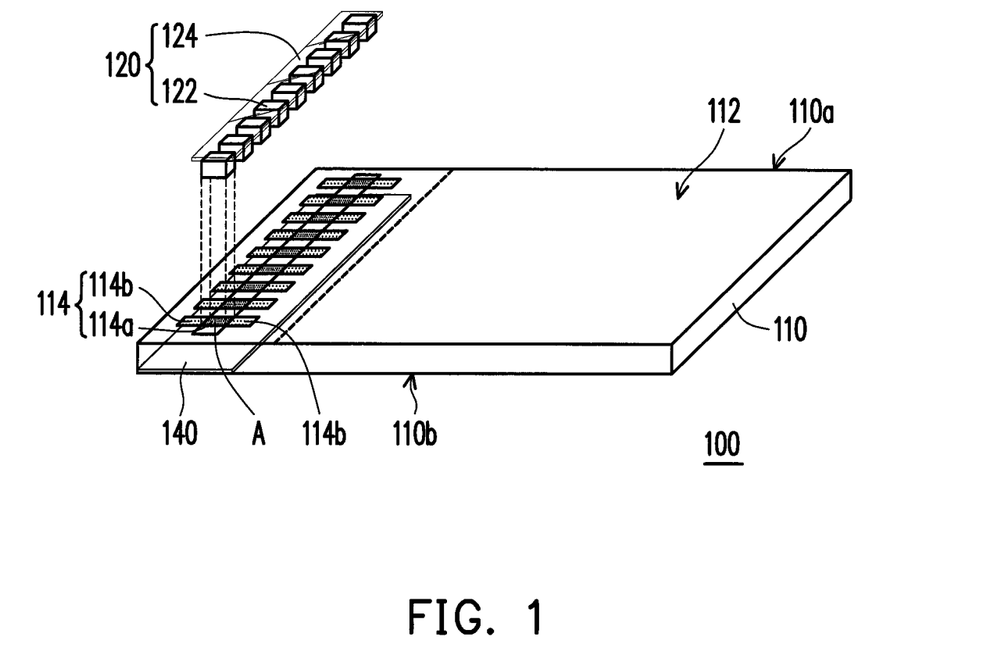
FIG. 1 is a schematic diagram of a light-guide module according to a first embodiment of the disclosure.
Figure 2:
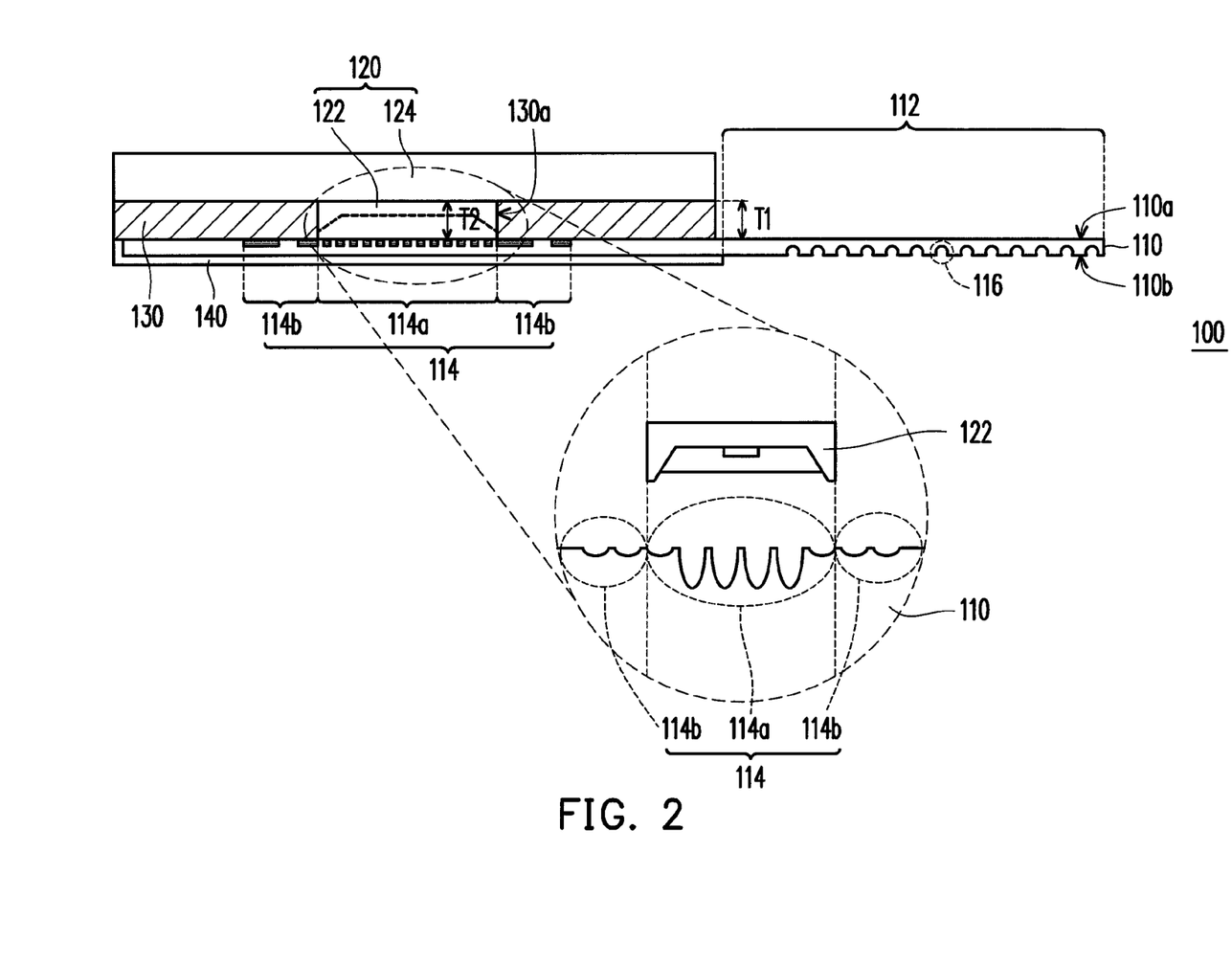
FIG. 2 is a cross-sectional view of a light-guide module according to the first embodiment of the disclosure.

FIG. 1 is a schematic diagram of a light-guide module according to a first embodiment of the disclosure, and FIG. 2 is a cross-sectional view of the light-guide module according to the first embodiment of the disclosure. Referring to FIG. 1 and FIG. 2, the light-guide module 100 of the embodiment includes a light-guide sheet 110 and a light source 120. The light-guide sheet 110 includes a light-emergent region 112 and a plurality of localized micro-structures 114, where the light-emergent region 112 and the localized micro-structures 114 are located on a first surface 110a of the light-guide sheet 110, and the localized micro-structures 114 are distributed except the light-emergent region 112. In the present embodiment, the localized micro-structures 114 are adjacent to the light-emergent region 112, though the disclosure is not limited thereto. The light source 120 includes a plurality of light-emitting devices 122 disposed on the first surface 110a, and lights emitted from the light-emitting devices 122 enter the light-guide sheet 110 through the localized micro-structures 114. In detail, the localized micro-structures 114 include a first region 114a having a plurality of arc grooves with the same or different aspect ratios (which are described later), and the first region 114a is a region in the localized micro-structures 114 that is covered by the light-emitting devices 122. Light-emitting surfaces of the light-emitting devices 122 face to or cover the localized micro-structures 114 of the first region 114a, and a light-emitting area (i.e. an area of the first region 114a covered by the light-emitting device 122) of each of the light-emitting devices 122 is A. It should be noticed that in the localized micro-structures 114 of the first region 114a covered by the light-emitting devices 122, an area occupied by the arc grooves having aspect ratios greater than 0.5 is substantially greater than or substantially equal to 0.5 A (for example, greater than or substantially equal to 0.6 A or greater than or substantially equal to 0.8 A). Moreover, the localized micro-structures 114 further include a second region 114b having a plurality of arc grooves with the same or different aspect ratios, and the second region 114b is a region in the localized micro-structures 114 that is not covered by the light-emitting devices 122. In the localized micro-structures 114 of the second region 114b that is not covered by the light-emitting devices 122, an area occupied by the arc grooves having aspect ratios greater than 0.5 is substantially smaller than or substantially equal to 0.7 A (for example, smaller than or substantially equal to 0.5 A).

In the present embodiment, a total area of the localized micro-structures 114 (i.e. a sum of the first region 114a and the second region 114b) is about 0.5-3 times of the light-emitting area A of the light-emitting devices 122 (i.e. 0.5 A-3 A).

According to FIG. 2, since the light-emitting devices 122 are disposed close to the first surface 110a of the light-guide sheet 110, the above area A is substantially the same to the light-emitting area of the light-emitting devices 122.

In the present embodiment, the light-guide sheet 110 is, for example, a flexible light-guide sheet, and a material thereof is, for example, polycarbonate (PC), polymethyl methacrylate (PMMA), polyethylene terephthalate (PET), cycloolefin polymer (COP) or fluorine or silicon-contained resin, etc., which are capable of transmitting light. The light-guide sheet 110 selectively has a second surface 110b opposite to the first surface 110a, and has a plurality of light-emergent micro-structures 116 distributed on the second surface 110b, where the light-emergent micro-structures 116 are disposed corresponding to the light-emergent region 112. Moreover, the light-guide module 100 may further include a reflective sheet 140 disposed on the second surface 110b, where the reflective sheet 140 is disposed corresponding to the localized micro-structures 114. The reflective sheet 140 can effectively reduce an amount of light leaving the light-guide sheet 110 through the second surface 110b, so as to enhance a whole output efficiency of the light-guide module 100. Moreover, the reflective sheet 140 is, for example, a silver reflective sheet, a white reflective sheet or other materials with a good reflectivity.

The localized micro-structures 114 and the light-emergent micro-structures 116 on the light-guide sheet 110 are, for example, fabricated through a laser processing method, and the used laser is, for example, a carbon dioxide laser, a Nd:YAG laser, or an excimer laser, etc. Certainly, those skilled in the art can use other processing methods, for example, molding, printing, screen printing, inkjet, or other mechanical processing methods to fabricate the localized micro-structures 114 and the light-emergent micro-structures 116.

Taking the laser processing as an example, when the first surface 110a of the light-guide sheet 110 is irradiated by a specific intensity of the laser light, arc grooves parallel to each other are formed on the first surface 110a, and a combination of the arc grooves is the localized micro-structures 114. Depths, arrangement spaces and arrangement patterns of the arc grooves are correlated to a laser intensity, a laser type, and irradiation times of the laser processing, and those skilled in the art can adjust the laser processing procedure according to the required depths, arrangement spaces and arrangement patterns of the arc grooves.

The processing method of the localized micro-structures 114 is described in detail in following experiments.

In the present embodiment, besides the light-emitting devices 122, the light source 120 may further include a circuit board 124, where the light-emitting devices 122 are disposed on the circuit board 124 and are electrically connected to the circuit board 124. For example, the light-emitting devices 122 can be a light-emitting diode (LED) package (for example, a top lighting type LED package or side lighting type LED package), the circuit board 124 can be a general printed circuit board (PCB), a metal core PCB, or a flexible PCB, which is not limited by the disclosure.

To ensure the light emitted from the light-emitting device 122 efficiently entering the light-guide sheet 110, the light-guide module 100 of the present embodiment may further include a light-leakage suppressing layer 130, where the light-leakage suppressing layer 130 is disposed on the first surface 110a except the light-emergent region 112 to cover the localized micro-structures 114 of the second region 114b, and the light-leakage suppressing layer 130 has a plurality of openings 130a to expose the localized micro-structures 114 of the first region 114a, where the light-emitting devices 122 are respectively embedded in the corresponding openings 130a. It should be noticed that the localized micro-structures 114 include a plurality of the arc grooves having the same or different aspect ratios, and in the localized micro-structures 114 of the first region 114a exposed by the openings 130a, an area occupied by the arc grooves having the aspect ratios greater than 0.5 is greater than or substantially equal to 0.5 A, and in the localized micro-structures 114 of the second regions 114b covered by the light-leakage suppressing layer 130, an area occupied by the arc grooves having the aspect ratios greater than 0.5 is smaller than or substantially equal to 0.7 A. Moreover, the light-leakage suppressing layer 130 is disposed between the circuit board 124 and the light-guide sheet 110.

As shown in FIG. 2, the opening 130a has a suitable length and width to facilitate partially or totally inlaying the light-emitting device 122, and a thickness T1 (i.e. a depth of the opening 130a) of the light-leakage suppressing layer 130 is, for example, greater than or substantially equal to a half of a thickness T2 of each of the light-emitting devices 122. In the present embodiment, the light-leakage suppressing layer 130 is a reflective plate (for example, a silver reflective plate), and a length and a width of the light-leakage suppressing layer 130 is, for example, slightly greater than or substantially equal to a length and a width of the light-emitting device 122, so that the light-emitting device 122 can be embedded in the opening 130a, and the thickness T1 of the light-leakage suppressing layer 130 can be substantially the same to the thickness T2 of each of the light-emitting devices 122, so that the light-emitting device 122 can be totally embedded in the opening 130a.

Second Embodiment

Figure 3A:
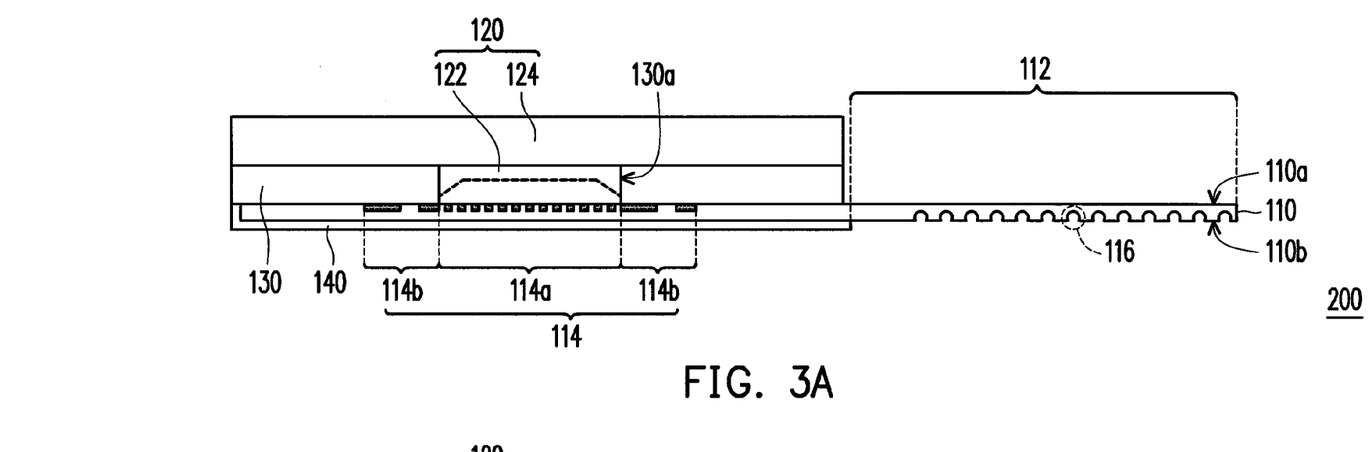
FIGS. 3A-3C are cross-sectional views of a light-guide module according to a second embodiment of the disclosure.
Figure 3B:
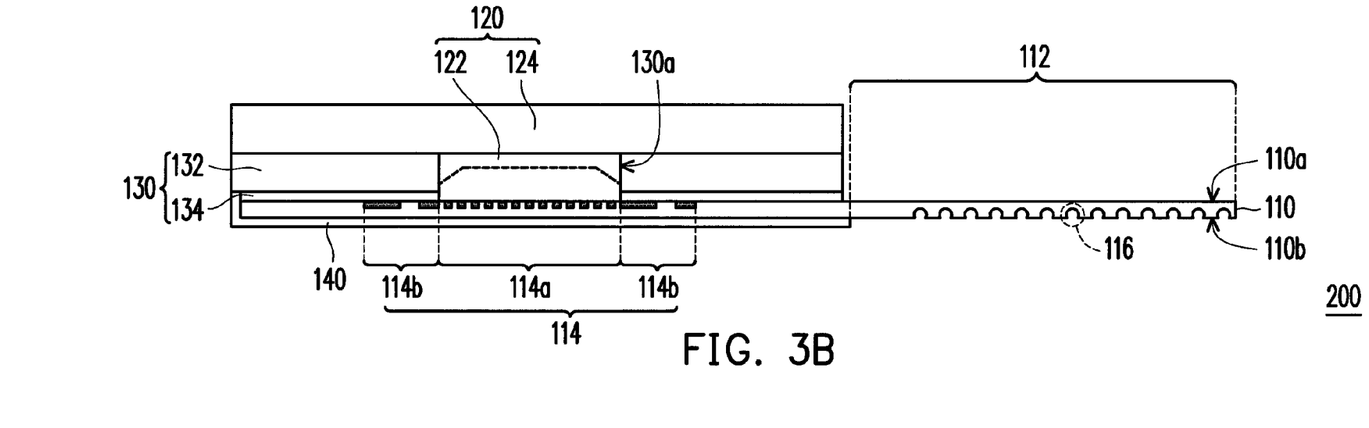
Figure 3C:
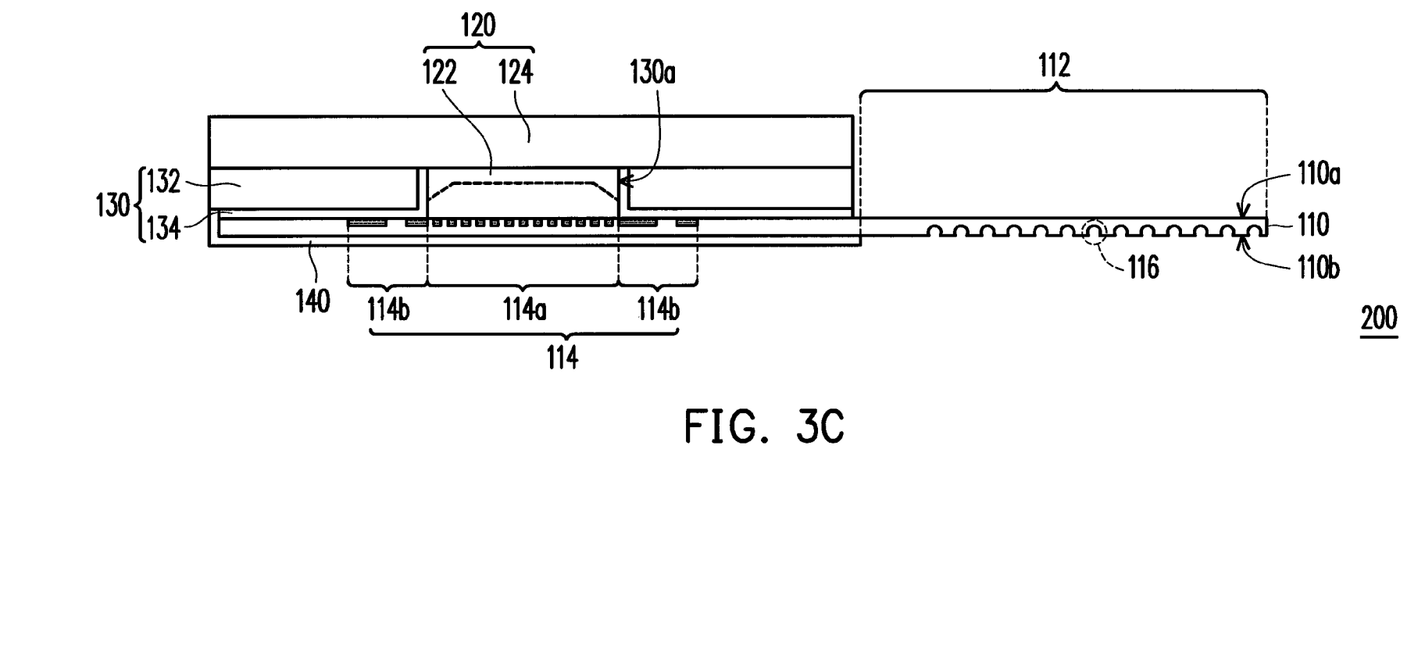

FIGS. 3A-3C are cross-sectional views of a light-guide module according to a second embodiment of the disclosure. Referring to FIGS. 3A-3B, the light-guide module 200 of the present embodiment is similar to the light-guide module 100 of the first embodiment, and a main difference there between is that the light-leakage suppressing layer 130 of the present embodiment is a supporting plate having the opening 130a (shown in FIG. 3A), or includes a supporting plate 132 having the opening 130a and a reflective layer 134 disposed between the light-guide sheet 110 and the supporting plate 132 (shown in FIG. 3B and FIG. 3C). It should be noticed that the reflective layer 134 of FIG. 3C extends to a sidewall of the opening 130a.

Third Embodiment

Figure 4A:
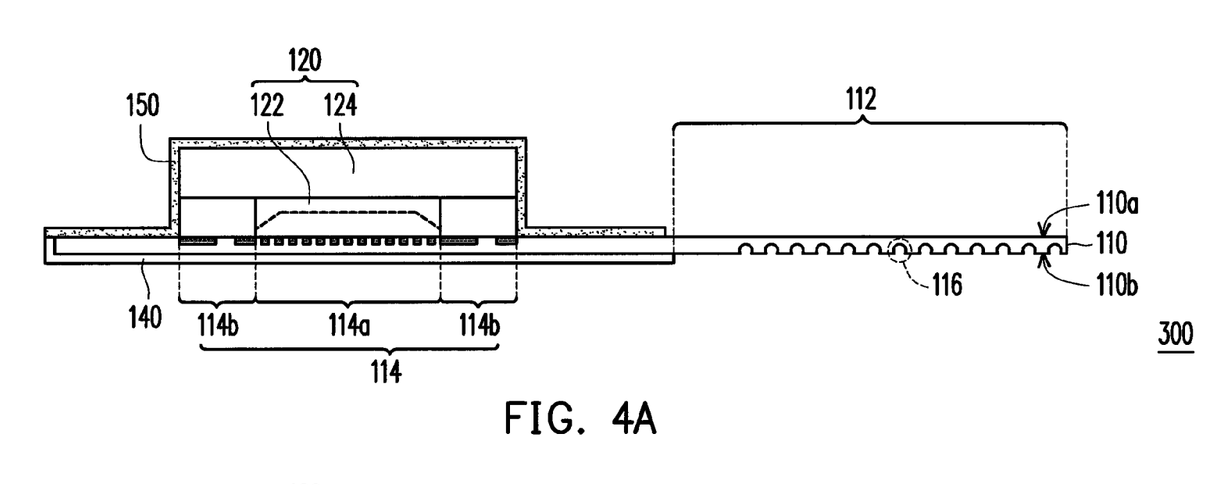
FIG. 4A and FIG. 4B are cross-sectional views of a light-guide module according to a third embodiment of the disclosure.
Figure 4B:
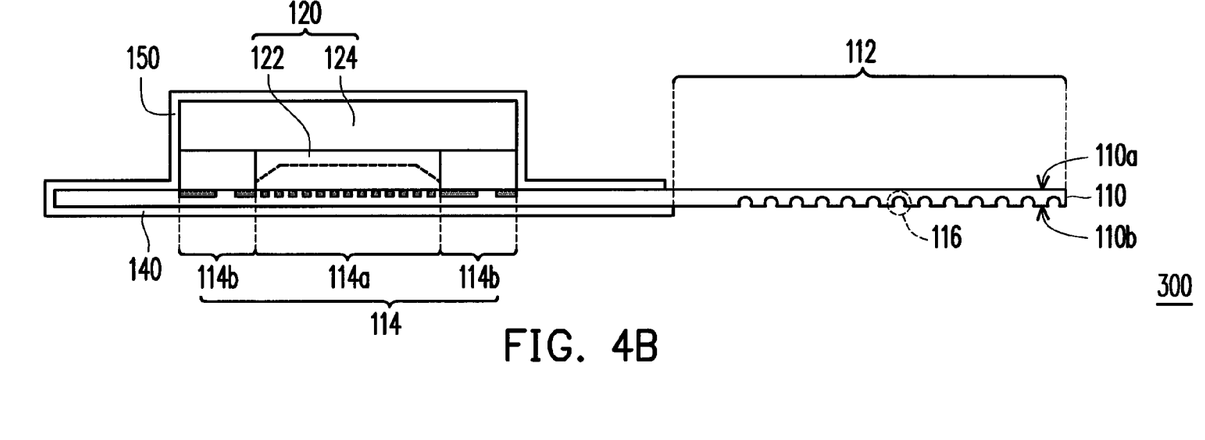

FIG. 4A and FIG. 4B are cross-sectional views of a light-guide module according to a third embodiment of the disclosure. Referring to FIG. 4A and FIG. 4B, the light-guide module 300 of the present embodiment is similar to the light-guide module 100 of the first embodiment, and a main difference there between is that the light-guide module 300 of the present embodiment does not have the light-leakage suppressing layer 130, but includes a function layer 150, where the function layer 150 covers the circuit board 124 and a part of the first surface 110a except the light-emergent region 112. In the present embodiment, the function layer 150 is, for example, a heat dissipation layer or a reflective layer.

If the function layer 150 is a heat dissipation layer, the function layer 150 can effectively conduct the heat of the light-emitting devices 122 and the circuit board 124. If the function layer 150 is a reflective layer, the function layer 150 can effectively reflect back the leaked light to the light-guide sheet 110. Now, a function of the function layer 150 is similar to that of the light-leakage suppressing layer 130, though a configuration position of the function layer 150 is different to that of the light-leakage suppressing layer 130 of the first embodiment.

It should be noticed that a material of the function layer 150 can be different (shown in FIG. 4A) or the same (shown in FIG. 4B) to the material of the reflective sheet 140. If the material of the function layer 150 is the same to the material of the reflective sheet 140, the function layer 150 and the reflective sheet 140 can be fabricated together. For example, the function layer 150 can be made of a material with good heat-dissipation and reflection properties such as aluminium, silver, or can be a heat dissipation tape with an aluminium-coated layer, etc.

Fourth Embodiment

Figure 5:
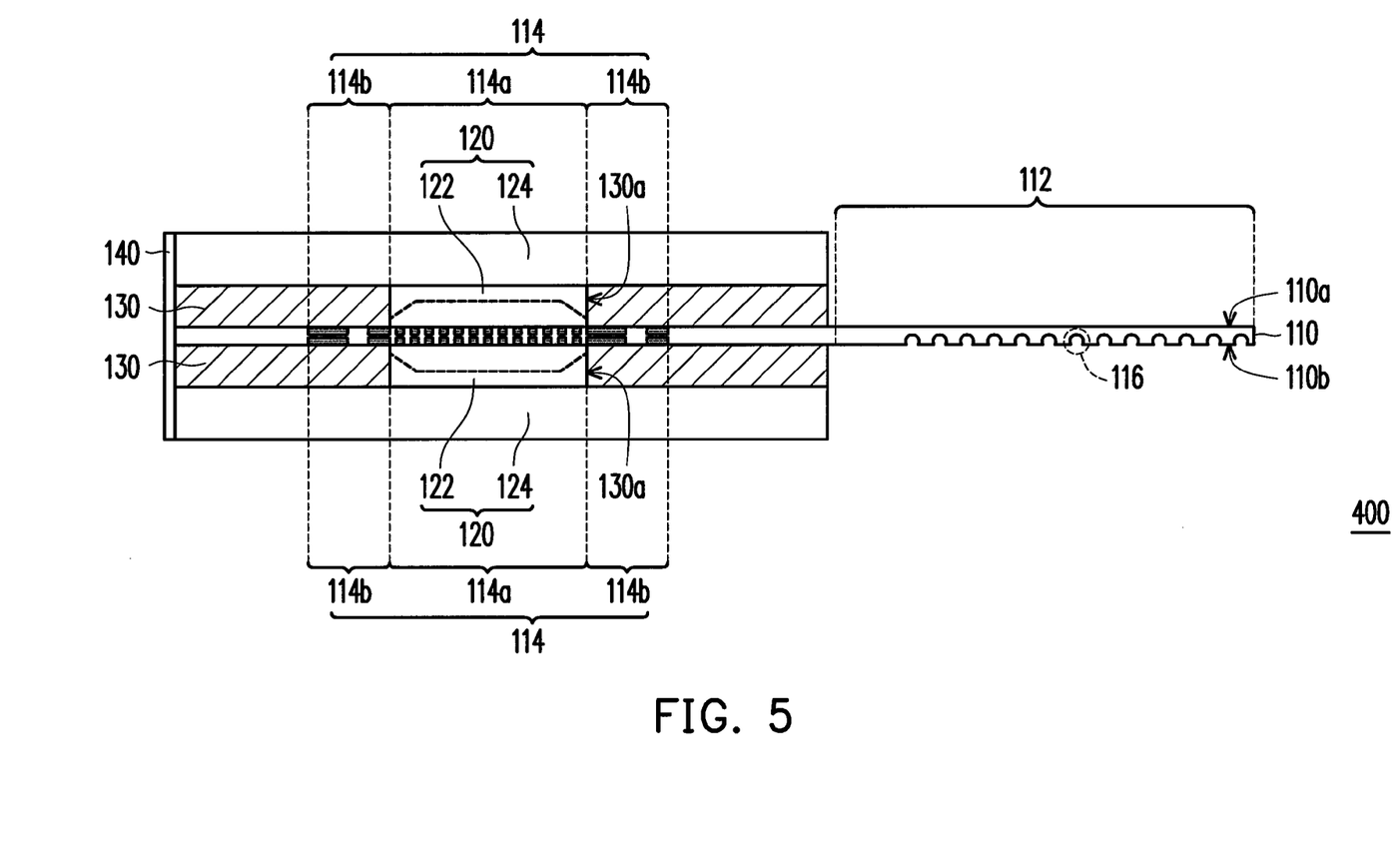
FIG. 5 is a cross-sectional view of a light-guide module according to a fourth embodiment of the disclosure.

FIG. 5 is a cross-sectional view of a light-guide module according to a fourth embodiment of the disclosure. Referring to FIG. 5, the light-guide module 400 of the present embodiment is similar to the light-guide module 100 of the first embodiment, and main differences there between are as follows. Both of the first surface 110a and the second surface 110b of the light-guide sheet 110 have the localized micro-structures 114, the light source 120 has a plurality of the light-emitting devices 122 respectively disposed on the first surface 110a and the second surface 110b, and the light emitted by each of the light-emitting devices 122 enters the light-guide sheet 110 through the corresponding localized micro-structure 114, where the localized micro-structures 114 on the first surface 110a and the second surface 110b satisfy following conditions:

In the localized micro-structures 114 of the first region 114a covered by the light-emitting devices 122, an area occupied by the arc grooves having the aspect ratios greater than 0.5 is greater than or substantially equal to 0.5 A (for example, greater than or substantially equal to 0.6 A or greater than or substantially equal to 0.8 A); and In the localized micro-structures 114 of the second regions 114b that are not covered by the light-emitting devices 122, an area occupied by the arc grooves having the aspect ratios greater than 0.5 is smaller than or substantially equal to 0.7 A (for example, smaller than or substantially equal to 0.5 A).

Moreover, a configuration position of the reflective sheet 140 is changed due to that both of the first surface 110a and the second surface 110b of the light-guide sheet 110 have the localized micro-structures 114, and in the present embodiment, since light enters the light-guide sheet 110 from both of the first surface 110a and the second surface 110b, the reflective sheet 140 is disposed at a side surface of the light-guide module 400, i.e. side surfaces of the circuit board 124 and the light-leakage suppressing layer 130 apart from the light-emergent region 112.

Fifth Embodiment

Figure 6:
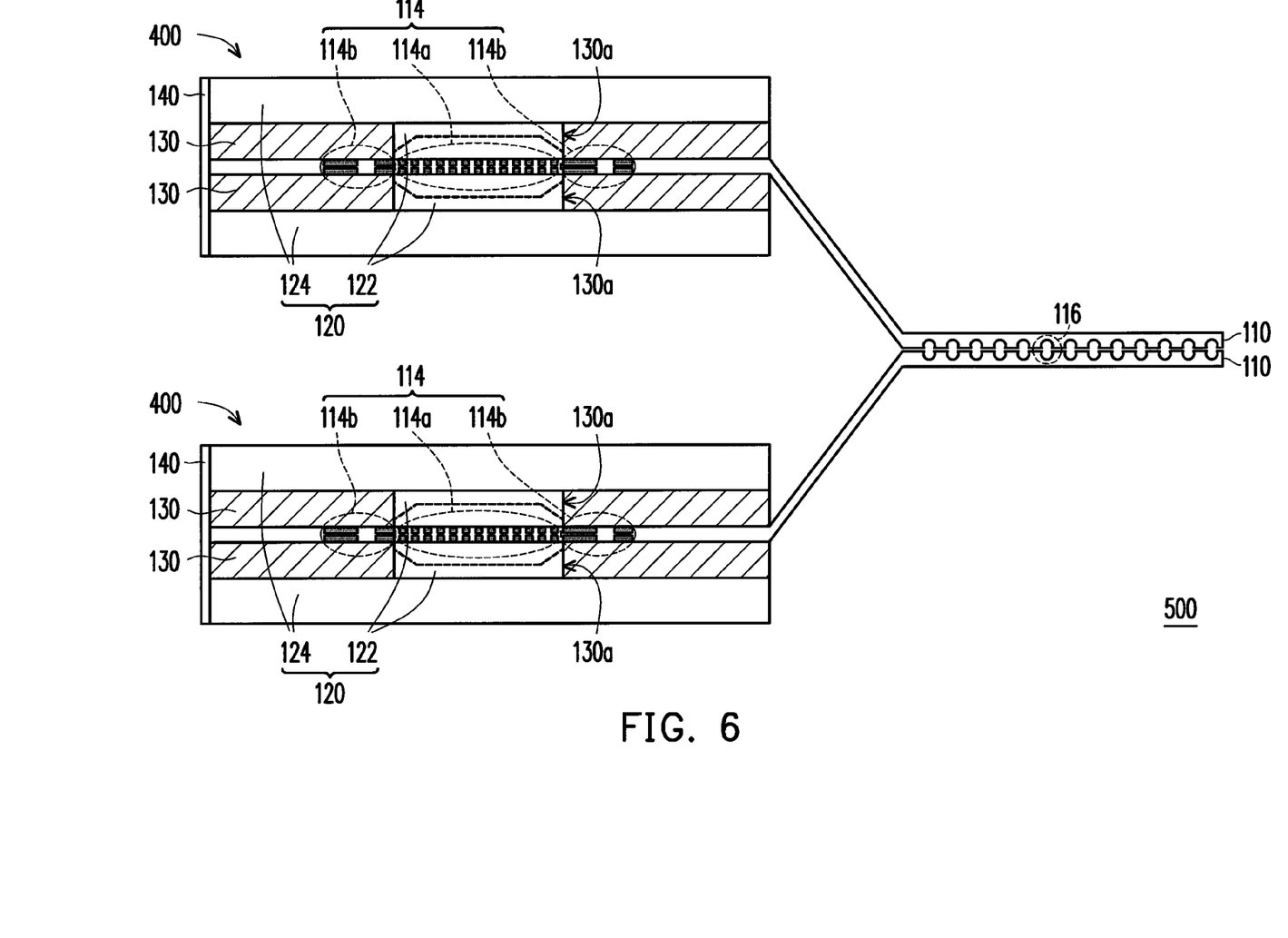
FIG. 6 is a cross-sectional view of a light-guide module according to a fifth embodiment of the disclosure.

FIG. 6 is a cross-sectional view of a light-guide module according to a fifth embodiment of the disclosure. Referring to FIG. 6, the light-guide module 500 of the present embodiment is similar to the light-guide module 400 of the fourth embodiment, and a main difference there between is that the light-guide module 500 of the present embodiment is formed by a plurality of light-guide module 400 stacked to each other.

Sixth Embodiment

Figure 7A:
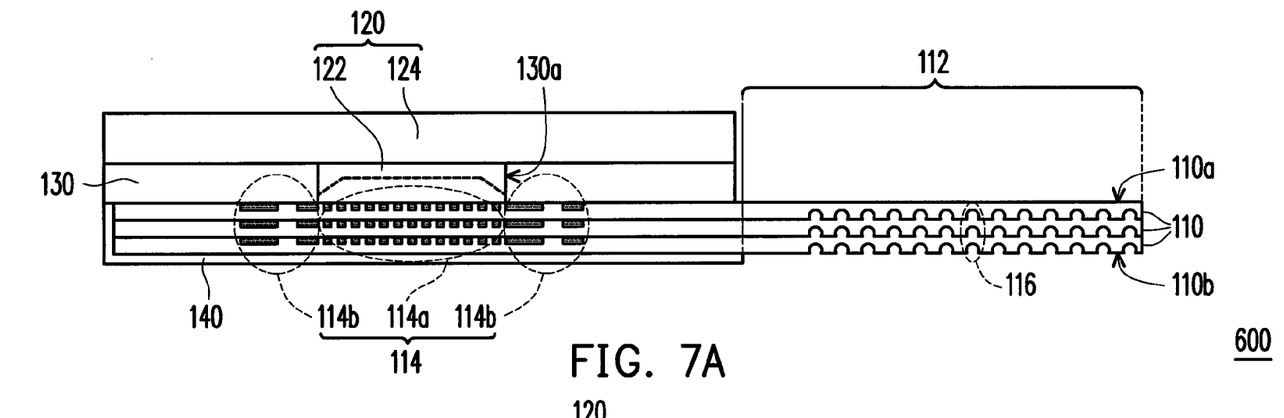
FIG. 7A and FIG. 7B are cross-sectional views of a light-guide module according to a sixth embodiment of the disclosure.
Figure 7B:
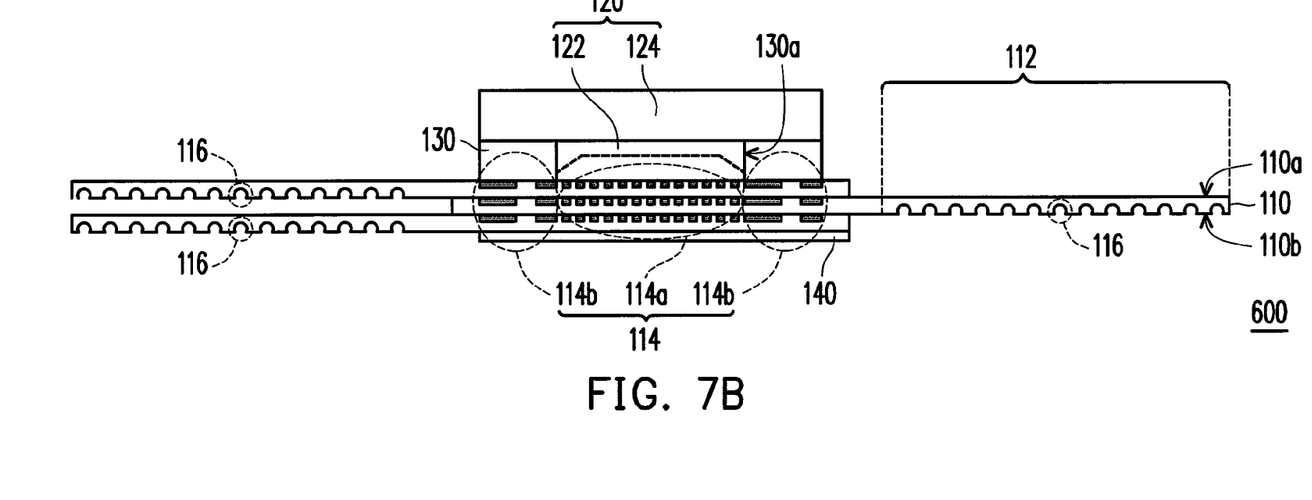

FIG. 7A and FIG. 7B are cross-sectional views of a light-guide module according to a sixth embodiment of the disclosure. Referring to FIG. 7A and FIG. 7B, the light-guide module 600 of the present embodiment is similar to the light-guide module 100 of the first embodiment, and a main difference there between is that in the light-guide module 600 of the present embodiment, a plurality of the light-guide sheets 110 are stacked, and the localized micro-structures 114 of the first region 114a in each of the light-guide sheets 110 can simultaneously correspond to the light-emitting surface of the light-emitting device 122, and an extending direction of each of the light-guide sheets 110 can be the same (shown in FIG. 7A) or different (shown in FIG. 7B).

Experiments

FIGS. 8A-8F are six experiments of the disclosure, which are used to describe fabrication methods of the arc grooves of the localized micro-structures 114. Referring to FIGS. 8A-8F, in the present embodiment, the light-emitting area of the light-emitting devices is fixed to 144 $mm^2$, and designs (six designs) of the localized micro-structures are adjusted to evaluate output effects of the light-guide module (a light-emergent luminance of the light-emergent region).

Figure 8A:
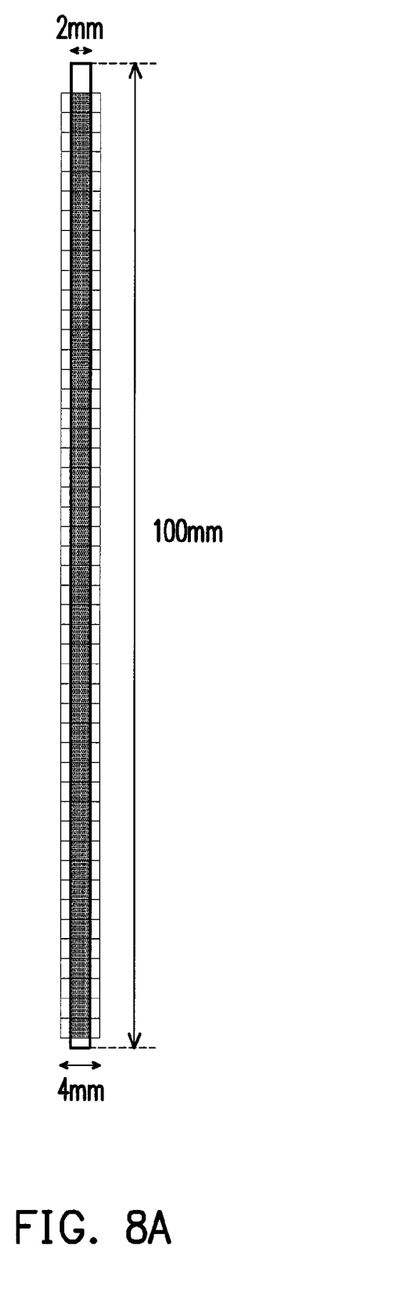
FIGS. 8A-8F are six experiments of the disclosure.

In FIG. 8A (an experiment A), a laser light with a width of 2 mm is used to irradiate the surface of the light-guide sheet, and the laser light is moved along a vertical direction of the light-guide sheet for about 100 mm to form one set of vertical arc groove on the light-guide sheet. Then, the light-guide sheet is rotated by 90 degrees. Thereafter, the laser light is moved along a horizontal direction of the light-guide sheet for about 4 mm, and such horizontal movement is repeated by 48 times to form 48 sets of horizontal arc grooves intersected to the vertical arc groove on the light-guide sheet. Since the laser light irradiates intersections of the vertical arc groove and the horizontal arc grooves by twice, arc grooves with aspect ratios greater than or substantially equal to 0.5 are generated at the intersections. Arc grooves with smaller aspect ratios are generated at the other regions of the vertical arc groove and the horizontal arc grooves that are not intersected.

Figure 8B:
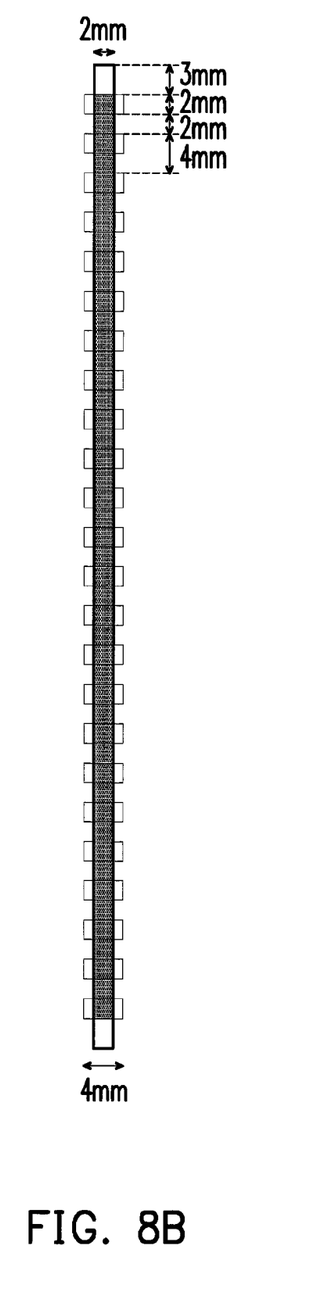

In FIG. 8B (an experiment B), the laser light with the width of 2 mm is used to irradiate the surface of the light-guide sheet, and the laser light is moved along the vertical direction of the light-guide sheet for about 100 mm to form one set of the vertical arc groove on the light-guide sheet. Then, the light-guide sheet is rotated by 90 degrees. Thereafter, the laser light is moved along the horizontal direction of the light-guide sheet for about 4 mm, and such horizontal movement is repeated by 24 times to form 24 sets of the horizontal arc grooves intersected to the vertical arc groove on the light-guide sheet, where a space between each two sets of the adjacent horizontal arc grooves is 2 mm. Arc grooves with aspect ratios greater than or substantially equal to 0.5 are generated at the intersections of the vertical arc groove and the horizontal arc grooves.

Figure 8C:
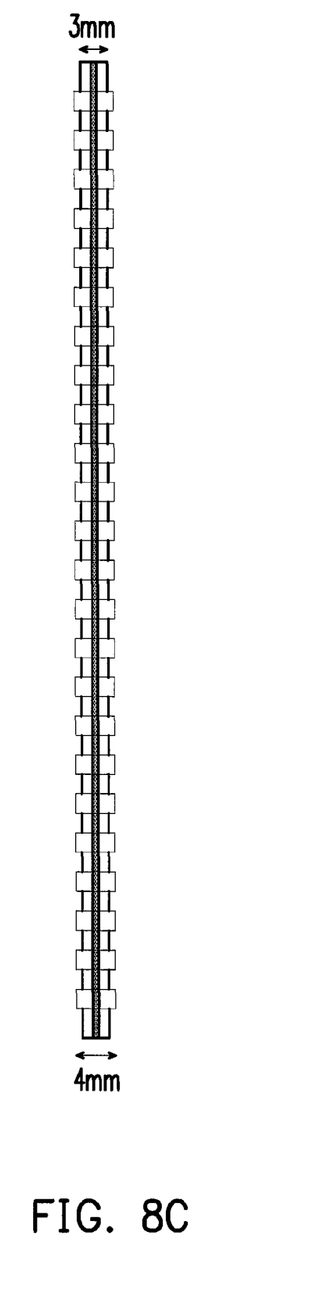

In FIG. 8C (an experiment C), the laser light with the width of 2 mm is used to irradiate the surface of the light-guide sheet, and the laser light is moved along the vertical direction of the light-guide sheet for about 100 mm, and such vertical movement is repeated by twice to form two sets of the vertical arc grooves with an overlapping width of 1 mm on the light-guide sheet (a total width of the two sets of the vertical arc grooves is 3 mm, and the arc groove with the aspect ratio greater than or substantially equal to 0.5 is generated by vertically moving the overlapping region). Then, the light-guide sheet is rotated by 90 degrees. Thereafter, the laser light is moved along the horizontal direction of the light-guide sheet for about 4 mm, and such horizontal movement is repeated by 24 times to form 24 sets of the horizontal arc grooves intersected to the vertical arc grooves on the light-guide sheet, where a space between each two sets of the adjacent horizontal arc grooves is 2 mm. Arc grooves with aspect ratios greater than or substantially equal to 0.5 are generated at the intersections of the vertical arc grooves and the horizontal arc grooves.

Figure 8D:
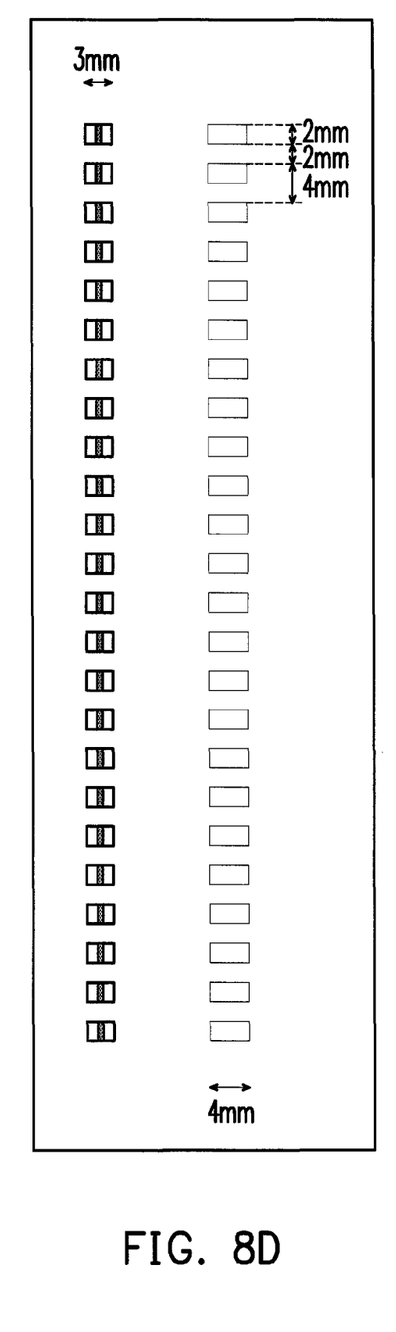

In FIG. 8D (an experiment D), the laser light with the width of 2 mm is used to irradiate the surface of the light-guide sheet, and the laser light is moved along the vertical direction of the light-guide sheet for about 2 mm, and such vertical movement is repeated by 48 times to form 24 sets of the vertical arc grooves with an overlapping width of 1 mm on the light-guide sheet (a total width of the vertical arc grooves is 3 mm, and the arc groove with the aspect ratio greater than or substantially equal to 0.5 is generated by vertically moving the overlapping region), where a space between each two sets of the adjacent vertical arc grooves is 2 mm. Then, the light-guide sheet is rotated by 90 degrees. Thereafter, the laser light is moved along the horizontal direction of the light-guide sheet for about 4 mm, and such horizontal movement is repeated by 24 times to form 24 sets of the horizontal arc grooves intersected to the vertical arc grooves on the light-guide sheet, where a space between each two sets of the adjacent horizontal arc grooves is 2 mm. Arc grooves with aspect ratios greater than or substantially equal to 0.5 are generated at the intersections of the vertical arc grooves and the horizontal arc grooves.

Figure 8E:
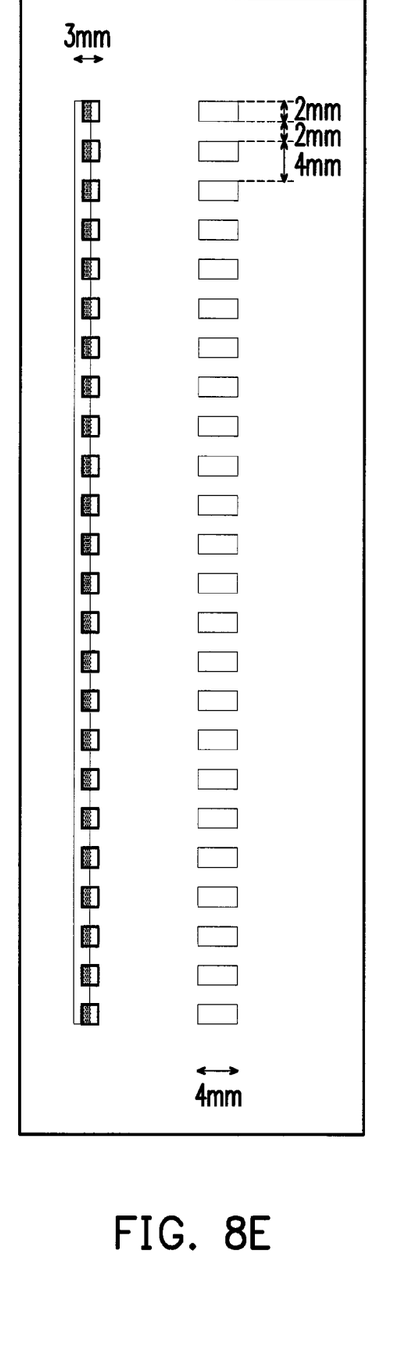

In FIG. 8E (an experiment E), the laser light with the width of 2 mm is used to irradiate the surface of the light-guide sheet, and the laser light is moved along the vertical direction of the light-guide sheet for about 100 mm to form one set of long vertical arc groove on the light-guide sheet. Then, the laser light is moved along the vertical direction of the light-guide sheet for about 2 mm, and such vertical movement is repeated by 24 times to form 24 sets of short vertical arc grooves on the light-guide sheet, where an overlapping width of each set of the short vertical arc groove and the long vertical arc groove is 1 mm (the arc grooves with the aspect ratios greater than or substantially equal to 0.5 are generated at the overlapping region), where a space between each two sets of the adjacent short vertical arc grooves is 2 mm. Then, the light-guide sheet is rotated by 90 degrees. Thereafter, the laser light is moved along the horizontal direction of the light-guide sheet for about 4 mm, and such horizontal move-ment is repeated by 24 times to form 24 sets of the horizontal arc grooves intersected to the vertical arc grooves (including the long and short vertical arc grooves) and 24 sets of horizontal arc grooves that are not intersected to the vertical arc grooves on the light-guide sheet. Arc grooves with aspect ratios greater than or substantially equal to 0.5 are generated at the intersections of the vertical arc grooves and the horizontal arc grooves.

Figure 8F:
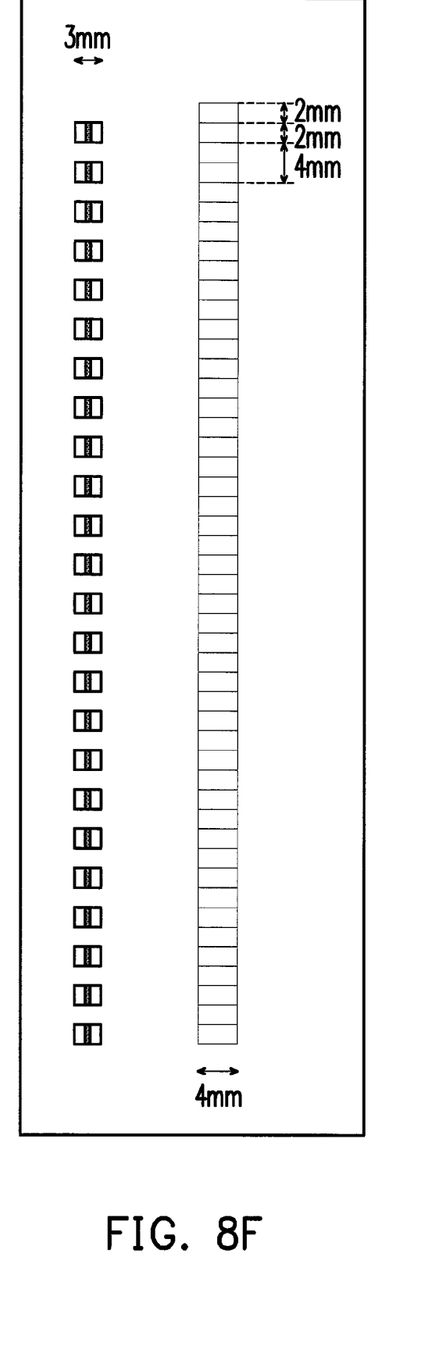

In FIG. 8F (an experiment F), the laser light with the width of 2 mm is used to irradiate the surface of the light-guide sheet, and the laser light is moved along the vertical direction of the light-guide sheet for about 2 mm, and such vertical movement is repeated by 48 times to form 24 sets of the vertical arc grooves with an overlapping width of 1 mm on the light-guide sheet (a total width of the vertical arc grooves is 3 mm, and the arc grooves with the aspect ratios greater than or substantially equal to 0.5 are generated at the overlapping region), where a space between each two sets of the adjacent vertical arc grooves is 2 mm. Then, the light-guide sheet is rotated by 90 degrees. Thereafter, the laser light is moved along the horizontal direction of the light-guide sheet for about 4 mm, and such horizontal movement is repeated by 48 times to form 24 sets of the horizontal arc grooves intersected to the vertical arc grooves and 24 sets of horizontal arc grooves that are not intersected to the vertical arc grooves on the light-guide sheet. Arc grooves with aspect ratios greater than or substantially equal to 0.5 are generated at the intersections of the vertical arc grooves and the horizontal arc grooves.

Design details of the localized micro-structures in the above six experiments (the experiment A, the experiment B, the experiment C, the experiment D, the experiment E, the experiment F) are as that shown in a following table one.

TABLE ONE

| Experiment | Light-emitting area A of light-emitting device (mm$^2$) | a1 | b | b1 | Light-emergent luminance (cd/m$^2$) |
|---|---|---|---|---|---|
| A | 144 | 2/3 | 5/3 | 2/3 | 22 |
| B | 144 | 2/3 | 1 | 0 | 42 |
| C | 144 | 1 | 4/3 | 1/3. | 35 |
| D | 144 | 1 | 0 | 0 | 45 |
| E | 144 | 1 | 1/3 | 0 | 50 |
| F | 144 | 1 | 4/3 | 0 | 50 |

Definitions of a1, b and b1 in the table one are as follows:

a1: a ratio between an area occupied by the arc grooves having aspect ratios greater than 0.5 in the localized micro-structures covered by the light-emitting devices (i.e. the first region) and A.

b: a ratio between an area occupied by the localized micro-structures that are not covered by the light-emitting devices (i.e. the second region) and A.

b1: a ratio between an area occupied by the localized micro-structures having aspect ratios greater than 0.5 in the localized micro-structures that are not covered by the light-emitting devices (i.e. the second region) and A.

According to the experiments A and B of the table one, it is known that the smaller the ratio b1 is, the higher the light-emergent luminance of the light-guide module is. Similarly, according to the experiments C and D of the table one, it is known that the smaller the ratio b1 is, the higher the light-emergent luminance of the light-guide module is.

According to the experiments B and D of the table one, it is known that the greater the ratio a1 is, the higher the light-emergent luminance of the light-guide module is.

According to the experiments E and F of the table one, it is known that when the ratio a1 approaches to 1, and the ratio b1 approaches to 0, the light-emergent luminance of the light-guide module is further enhanced.

In summary, the light-guide module of the disclosure can be applied for large-area planar light source illumination, for example, medical illumination, backlight source of display, front light source, billboard illumination, flexible lamp, light-emitting thin-film decoration and light-emitting brand, etc. Applications of the disclosure in medical illumination are, for example, neonatal jaundice illumination, acne treatment, skin aging slowing, wound repair and regeneration, hair growth, pain relief, seasonal depression, jet lag adjustment, dental light therapy, etc. The disclosure can also be applied to a luminous pad or a luminous blanket, which can be attached to the skin of a neonate to achieve uniform light therapy of large-area jaundice, and skin-contacting illuminometer and a jaundice reflection color measurement probe can be built therein to construct a feedback control system for jaundice therapy. Moreover, the disclosure can also be applied in a three-dimensional illumination system, which provides uniform illumination of a specific area on face skin according to a face outline, so as to quickly cure a laser wound. Moreover, the disclosure can be applied to a transparent illumination system, which avails observing a wound healing status during light therapy, and implementing light condition feedback control.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. A light-guide module, comprising:
   a light-guide sheet, comprising a light-emergent region and a plurality of localized micro-structures, wherein the light-emergent region and the localized micro-structures are located on a first surface of the light-guide sheet, and the localized micro-structures are distributed except the light-emergent region, the localized micro-structures comprise a first region and have a plurality of arc grooves;
   a light source, comprising a plurality of light-emitting devices disposed on the first surface, wherein lights emitted from the light-emitting devices enter the light-guide sheet through the localized micro-structures, a light-emitting area of each of the light-emitting devices is A, and the localized micro-structures satisfy a following condition:
   in the localized micro-structures of the first region covered by the light-emitting devices, an area occupied by the arc grooves having aspect ratios greater than 0.5 is greater than or substantially equal to 0.5 A.

2. The light-guide module as claimed in claim 1, wherein the localized micro-structures further comprise a second region and have a plurality of arc grooves, and the localized micro-structures satisfy a following condition:
   in the localized micro-structures of the second region that is not covered by the light-emitting devices, an area occupied by the arc grooves having aspect ratios greater than 0.5 is smaller than or substantially equal to 0.7 A.

3. The light-guide module as claimed in claim 2, further comprising a light-leakage suppressing layer disposed on the first surface except the light-emergent region to cover the localized micro-structures of the second region, wherein the light-leakage suppressing layer has a plurality of openings to expose the localized micro-structures of the first region, and each of the light-emitting devices is embedded in the corresponding opening.

4. The light-guide module as claimed in claim 3, wherein a thickness of the light-leakage suppressing layer is substantially the same to a thickness of each of the light-emitting devices.

5. The light-guide module as claimed in claim 3, wherein a thickness of the light-leakage suppressing layer is greater than or substantially equal to a half thickness of each of the light-emitting devices.

6. The light-guide module as claimed in claim 3, wherein the light source further comprises a circuit board, the light-emitting devices are disposed on the circuit board and are electrically connected to the circuit board, and the light-leakage suppressing layer is disposed between the circuit board and the light-guide sheet.

7. The light-guide module as claimed in claim 3, wherein the light-leakage suppressing layer is a reflective plate.

8. The light-guide module as claimed in claim 3, wherein the light-leakage suppressing layer is a supporting plate.

9. The light-guide module as claimed in claim 3, wherein the light-leakage suppressing layer comprises:
   a supporting plate; and
   a reflective layer, located between the light-guide sheet and the supporting plate.

10. The light-guide module as claimed in claim 1, wherein the light-guide sheet has a second surface opposite to the first surface, and the light-guide sheet has a plurality of light-emergent micro-structures distributed on the second surfaces, and the light-emergent micro-structures are distributed corresponding to the light-emergent region.

11. The light-guide module as claimed in claim 9, further comprising a reflective sheet disposed on the second surface, wherein the reflective sheet is disposed corresponding to the localized micro-structures.

12. The light-guide module as claimed in claim 1, wherein the light source further comprises a circuit board, the light-emitting devices are disposed on the circuit board and are electrically connected to the circuit board, and the light-emitting devices are located between the circuit board and the light-guide sheet.

13. The light-guide module as claimed in claim 12, further comprising a function layer, wherein the function layer covers the circuit board and a part of the first surface except the light-emergent region, and the function layer is a heat dissipation layer or a reflective layer.

14. The light-guide module as claimed in claim 1, wherein the light-guide sheet is a flexible light-guide sheet.

15. The light-guide module as claimed in claim 1, wherein a total area occupied by the localized micro-structures ranges from about 0.5 A to about 3 A.

* * * * *